United States Patent
Oh et al.

(10) Patent No.: US 11,638,432 B2
(45) Date of Patent: May 2, 2023

(54) **FEED ADDITIVE COMPRISING *BACILLUS SUBTILIS* AND *BACILLUS LICHENIFORMIS*, A FEED COMPOSITION COMPRISING THE FEED ADDITIVE AND A METHOD FOR PRODUCING THE FEED ADDITIVE**

(71) Applicant: CJ CHEILJEDANG CORPORATION, Seoul (KR)

(72) Inventors: Eun Seon Oh, Seongnam-si (KR); Yu Jin Kim, Suwon-si (KR); Min Ah Park, Suwon-si (KR); Seo Hyung Woo, Suwon-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 16/877,874

(22) Filed: May 19, 2020

(65) Prior Publication Data
US 2020/0275680 A1 Sep. 3, 2020

Related U.S. Application Data

(63) Continuation of application No. 15/745,087, filed as application No. PCT/KR2017/008446 on Aug. 4, 2017, now abandoned.

(30) Foreign Application Priority Data

Jul. 12, 2017 (KR) .......................... 10-2017-0088646

(51) Int. Cl.
| | | |
|---|---|---|
| A23K 10/18 | (2016.01) | |
| A23K 50/10 | (2016.01) | |
| C12N 1/20 | (2006.01) | |
| C12R 1/10 | (2006.01) | |
| C12R 1/125 | (2006.01) | |

(52) U.S. Cl.
CPC .............. *A23K 10/18* (2016.05); *A23K 50/10* (2016.05); *C12N 1/205* (2021.05); *C12R 2001/10* (2021.05); *C12R 2001/125* (2021.05)

(58) Field of Classification Search
CPC ............ A23K 10/18; C12R 1/10; C12R 1/125
See application file for complete search history.

(56) References Cited

U.S. PATENT DOCUMENTS

2005/0271643 A1   12/2005   Sorokulova et al.

FOREIGN PATENT DOCUMENTS

| CN | 102283321 B | 8/2012 |
|---|---|---|
| CN | 102640855 A | 8/2012 |
| CN | 103918951 A | 7/2014 |

(Continued)

OTHER PUBLICATIONS

Kritas et al., "Effect of Bacillus licheniformis and Bacillus subtilius Supplementation of Ewe's Feed on Sheep Milk Production and Young Lamb Mortality", J. Vet. Med. A 53, (2006), pp. 170-173. (Year: 2006).*

(Continued)

*Primary Examiner* — Elizabeth Gwartney
(74) *Attorney, Agent, or Firm* — Knobbe, Martens, Olson & Bear, LLP

(57) ABSTRACT

The present invention relates to a feed additive comprising a *Bacillus subtilis* strain and a *Bacillus licheniformis* strain, a feed composition comprising the feed additive, and a method for producing the feed additive.

3 Claims, 5 Drawing Sheets
Specification includes a Sequence Listing.

(56) References Cited

FOREIGN PATENT DOCUMENTS

| CN | 103911323 B | 6/2016 |
|---|---|---|
| EP | 3662759 A1 | 6/2020 |
| KR | 10-2001-0077679 A | 8/2001 |
| KR | 10-0351754 B1 | 11/2002 |
| KR | 10-0643375 B1 | 11/2006 |
| KR | 10-2011-0102172 A | 9/2011 |
| KR | 10-2015-0085410 A | 7/2015 |
| KR | 10-1721900 B1 | 3/2017 |
| RU | 2437563 C | 12/2011 |
| WO | 2011/115306 A1 | 9/2011 |
| WO | 2019/027073 A1 | 2/2019 |

OTHER PUBLICATIONS

Yu Jin Kim, "Dramatic increase of milk fat via CJ's technology", Monthly Magazine of Dairy, vol. 171—9 pages (May 2017).
International Search Report of corresponding PCT Application No. PCT/KR2017/008446—8 pages (dated Apr. 11, 2018).
Notice of Allowance of corresponding Korean Patent Application No. 10-2017-0088646—7 pages (dated Dec. 21, 2018).
Wang et al., "The effect of probiotic BioPlus 2B on growth performance, dry matter and nitrogen digestibility and slurry noxious gas emission in growing pigs", Livestock Science, vol. 120—8 pages (2009).
FEEDAP, "Safety and efficacy of BioPlus 2B (Bacillus subtillis DSM 5750 and Bacillus licheniformis DSM 5749) as a feed additive for sows, piglets, pigs for fattening, turkeys for fattening and calve", EFSA Journal, vol. 14, No. 9—19 pages (2016).
Office Action of corresponding Japanese Patent Application No. 2018-501973—3 pages (dated Aug. 13, 2019).
Extended European Search Report of European Patent Application No. 17825096.5—7 pages (dated Feb. 1, 2021).
Eom et al., "Inhibition of *Bacillus cereus* Growth and Toxin Production by *Bacillus amyloliquefaciens* RD7-7 in Fermented Soybean Products", J. Microbiol. Biotechnol. (2016), 26(1), 44-55.
Sim et al., "Antipathogenic Activity of *Bacillus amyloliquefaciens* Isolated from Korean Traditional Rice Wine", Microbiol. Biotechnol. Lett. (2016), 44(1), 98-105.
EFSA FEEDAP Panel (EFSA Panel on Additives and Products or Substances used in Animal Feed), 2016. Scientific opinion on the safety and efficacy of BioPius 2B® (*Bacillus subtilis* DSM 5750 and *Bacillus licheniformis* DSM 5749) as a feed additive for sows, piglets, pigs for fattening, turkeys for fattening and calves. EFSA Journal 2016;14(9):4558, 19 pp. doi:10.2903/j.efsa.2016.4558.
Office Action in Chinese Application No. 201780002557.0 dated Oct. 11, 2021 in 16 pages.
Office Action in Vietnamese Application No. 1201800400 dated Nov. 29, 2021 in 4 pages.

* cited by examiner

[Fig. 1]
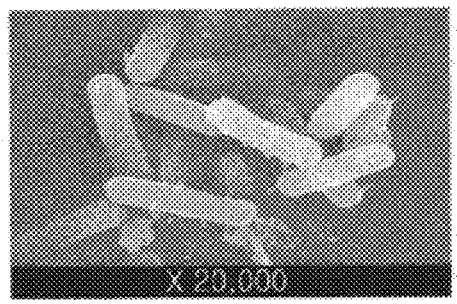
Bacillus licheniformis
CJBL215
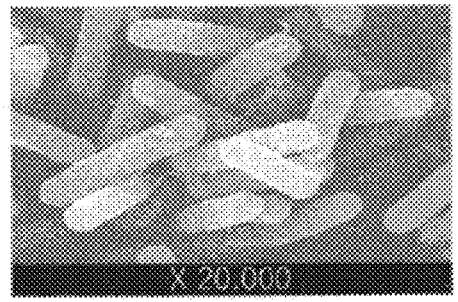
Bacillus licheniformis
CJBL219
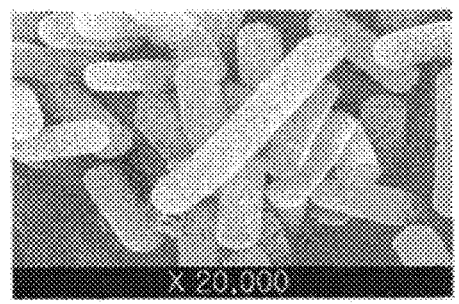
Bacillus subtilis
CJBS62
[Fig. 2]
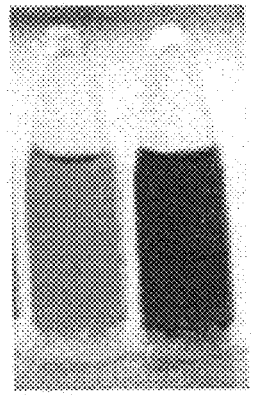
Control  Lactate-
        consuming
        strain

[Fig. 3]
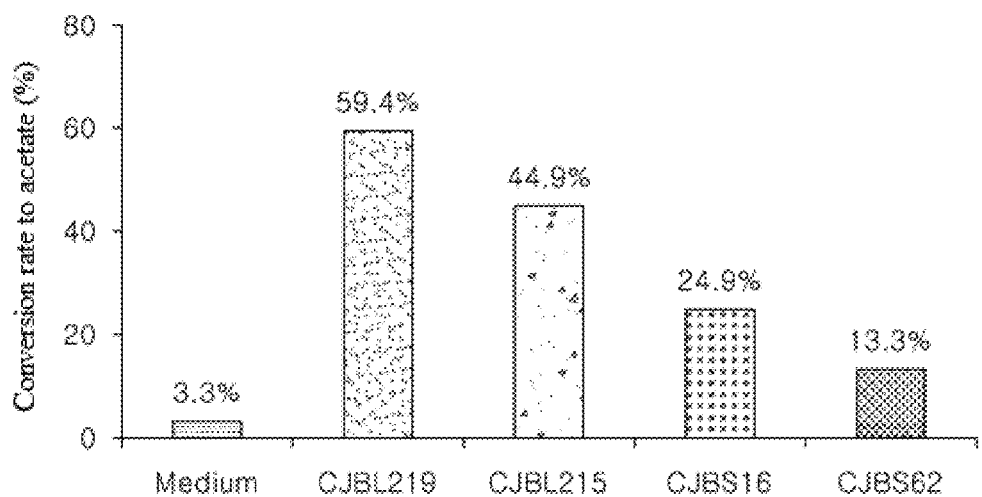
[Fig. 4]
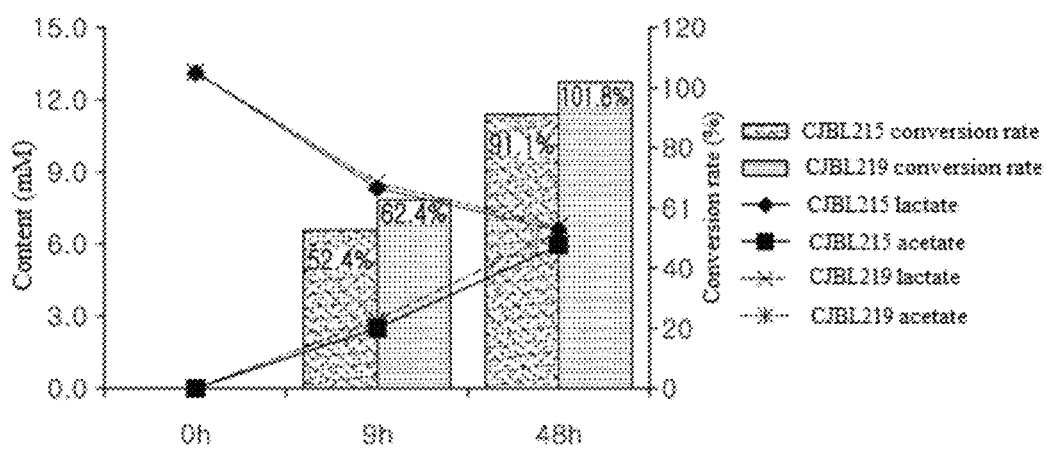

[Fig. 5]
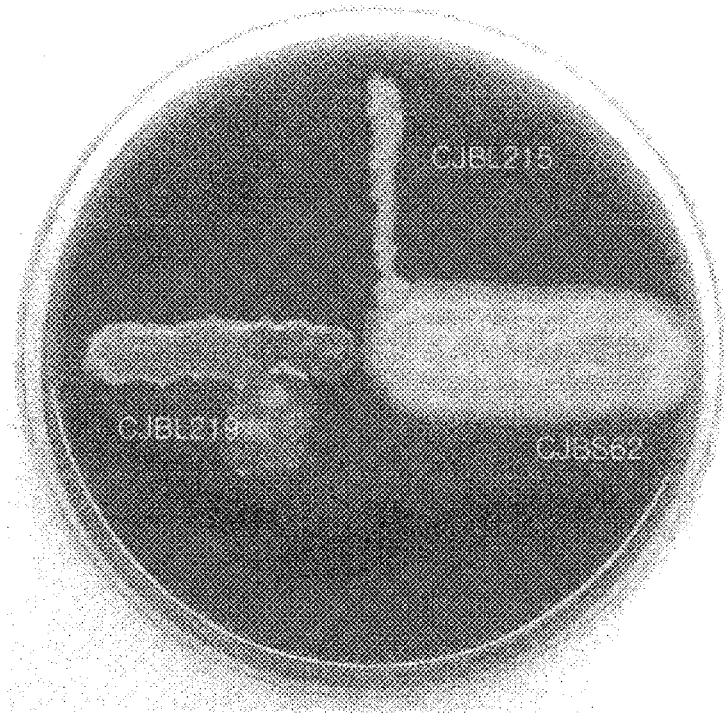
[Fig. 6]
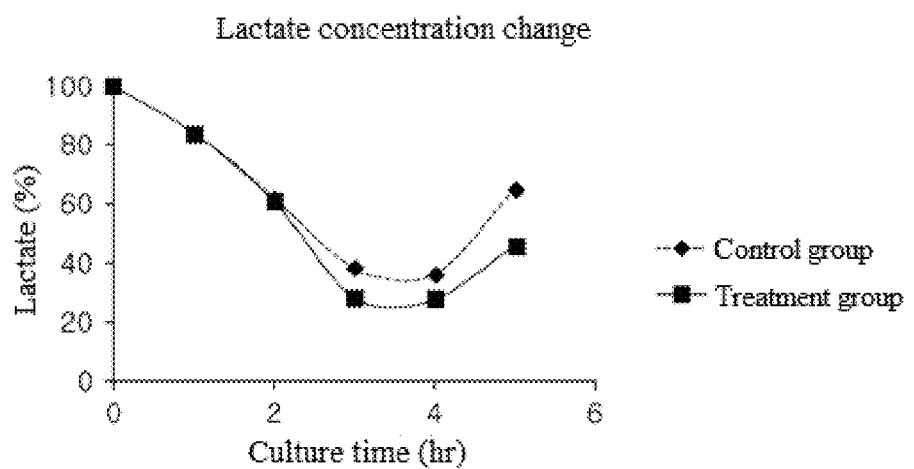

[Fig. 7]
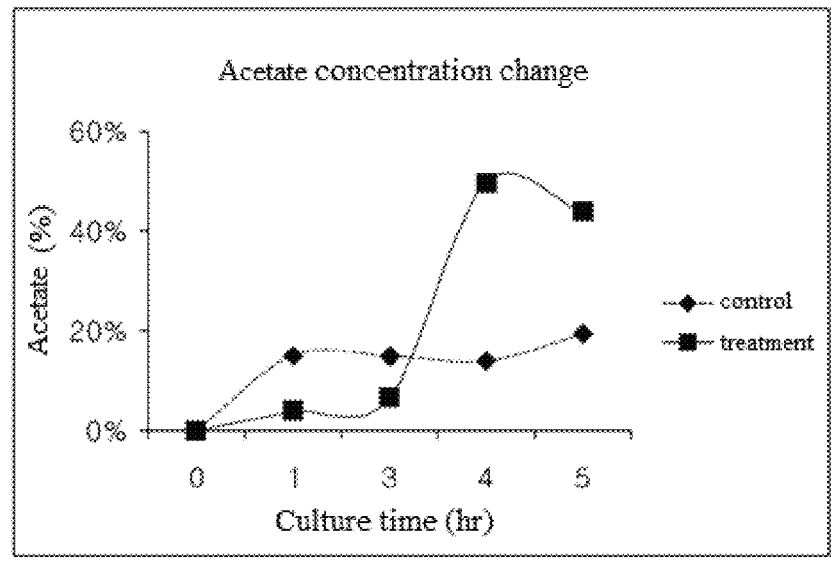
[Fig. 8]
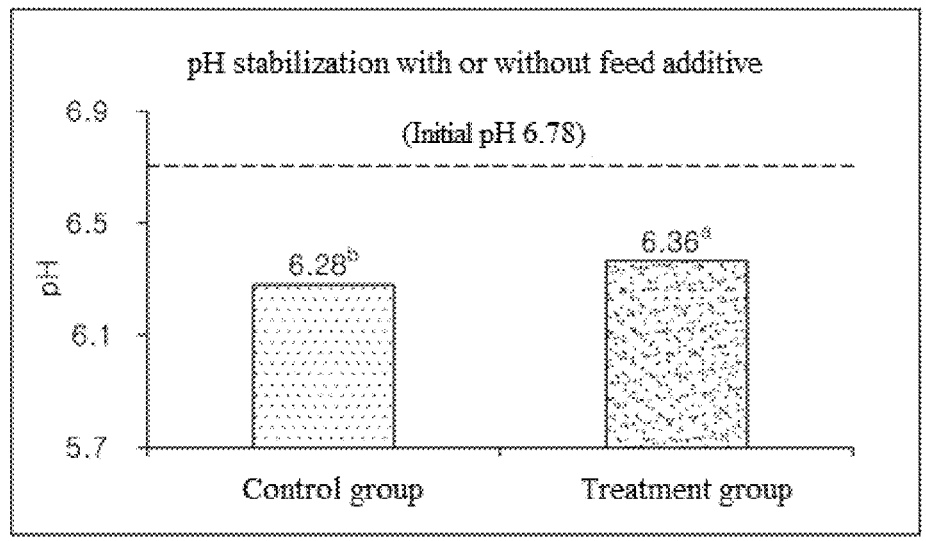

[Fig. 9]
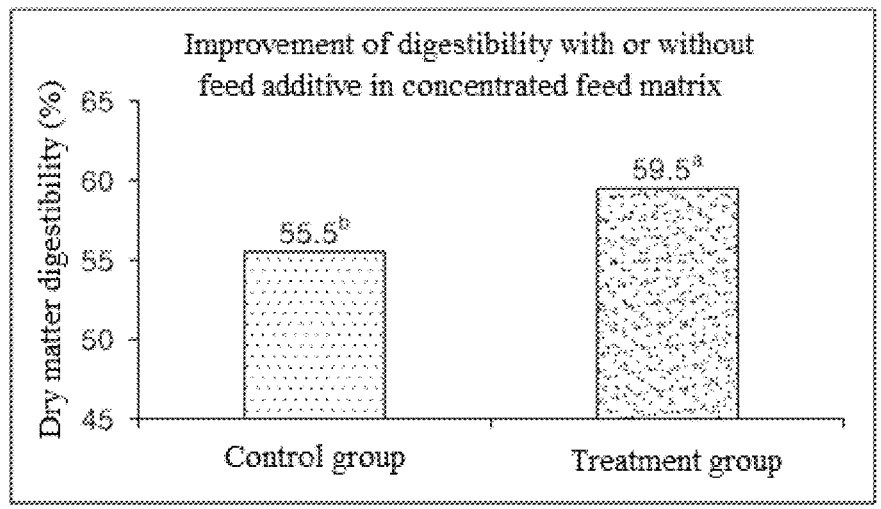
[Fig. 10]
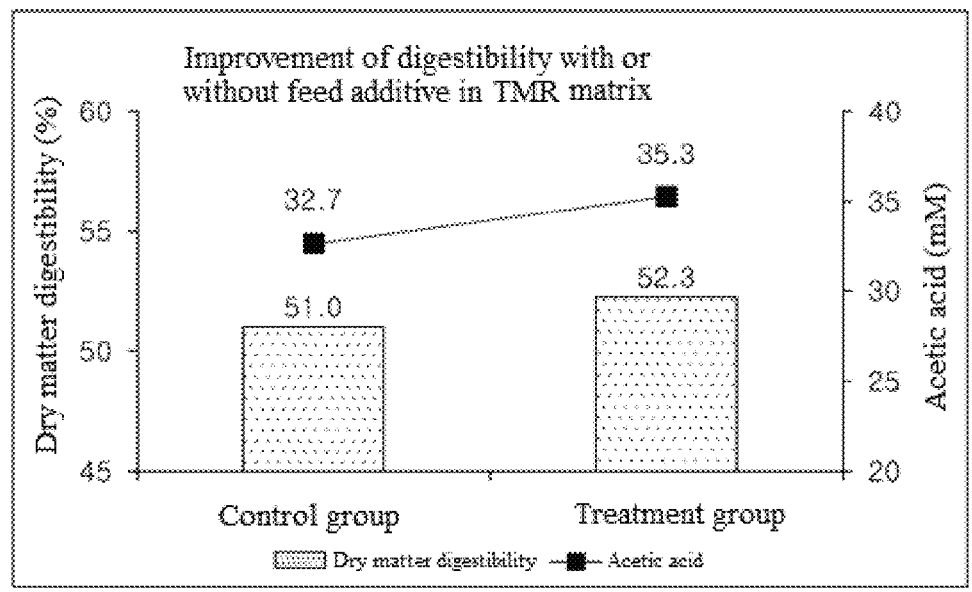

FEED ADDITIVE COMPRISING *BACILLUS SUBTILIS* AND *BACILLUS LICHENIFORMIS*, A FEED COMPOSITION COMPRISING THE FEED ADDITIVE AND A METHOD FOR PRODUCING THE FEED ADDITIVE

REFERENCE TO SEQUENCE LISTING

The present application is being filed along with a Sequence Listing in electronic format. The Sequence Listing is provided as a file entitled 34835491_1.TXT, created and last modified on May 18, 2020, which is 6.65 Kb in size. The information in the electronic format of the Sequence Listing is incorporated herein by reference in its entirety.

STATEMENT REGARDING PRIOR DISCLOSURES BY THE INVENTOR OR A JOINT INVENTOR UNDER 37 CFR 1.77(b)(6)

An article titled "Dramatic increase of milk fat via CJ's technology" was published on May 2017 as part of "Monthly Magazine of Dairy, Vol. 171." The article discloses subject matter relating to the present application. The sole author of the article, Yu Jin Kim, is a joint inventor. A copy of the article is submitted with an Information Disclosure Statement filed Jan. 15, 2018.

TECHNICAL FIELD

The present invention relates to a feed additive comprising a *Bacillus subtilis* strain and a *Bacillus licheniformis* strain, a feed composition comprising the feed additive, and a method for producing the feed additive.

BACKGROUND ART

Forage for ruminants, such as cattle, accounts for about 20% of feeds for beef cattle and about 60% of feeds for dairy cattle. After ingestion, forage is degraded by microorganisms and essential nutrients and energy are absorbed in the rumen, also known as the first stomach. From a nutritional/physiological point of view, ruminants ingest considerable amounts of protein, energy, fatty acids, minerals, and vitamins, which are essential to microorganisms inhabiting the rumen and the tissues of the animals, from forage. Forage takes the form of fresh grass, dry grass or silage. Dry forage contains ≥20-30% of crude fiber. Forage is composed of hemicellulose, lignin, and cellulose that are relatively difficult to degrade. A great deal of research has been conducted on methods for increasing the digestibility of forage to enhance the value of feeds. Representative examples of such methods include physical treatment methods (immersion, pulverization, pressure steam treatment, expansion, gamma-ray irradiation, and pelletizing), chemical treatment methods (sodium hydroxide, urea, ammonia, lime, calcium hydroxide, potassium hydroxide, sodium carbonate, chlorine, ozone, hydrogen peroxide, etc.), and biological treatment methods (fermentation, enzymatic modification, and silage, etc.). However, the physical treatment methods involve high processing costs. The chemical treatment methods incur increased processing costs and pose danger during handling. The chemical treatment methods also cause soil contamination or affect the normal physiological functioning of animals. For these reasons, use of the physical and chemical treatment methods is avoided. Thus, biological treatment methods based on the use of cellulolytic enzymes or the addition of microorganisms producing large amounts of such enzymes are mainly used. Particularly, much research has focused on increasing the degradation rate of cellulose.

Forage is fed in combination with concentrated feeds to dairy cattle and beef cattle to replenish a necessary amount of energy and to improve the productivity of milk and beef. Concentrated feeds are small in volume and high in energy content. Concentrated feeds are easily digestible compared to forage. However, feeding of large amounts of concentrated feeds increases the concentration of lactate in the course of starch degradation, leading to a significant decrease in the rumen pH. The decreased rumen pH adversely affects the growth of beneficial microorganisms and leads to acidosis, causing reduced feed intake, maldigestion, severe hypohydration, and diarrhea.

There is thus a need to develop a feed additive highly capable of degrading cellulose and lactate.

PRIOR ART DOCUMENTS

Patent Documents

Korean Patent No. 10-1721900

DISCLOSURE

Technical Problem

It is one object of the present invention to provide a feed additive comprising a *Bacillus subtilis* strain and a *Bacillus licheniformis* strain that is helpful in improving milk fat and is useful in enhancing milk yield.

It is another object of the present invention to provide a feed composition comprising the feed additive comprising a *Bacillus subtilis* strain and a *Bacillus licheniformis* strain.

Technical Solution

Hereinafter, embodiments of the present invention will be described in detail. It should be noted that descriptions of details apparent to those skilled in the art will be omitted for clarity.

One embodiment of the present invention provides a feed additive for enhancing milk fat and milk yield comprising a *Bacillus subtilis* strain and a *Bacillus licheniformis* strain.

Any strain belonging to *Bacillus subtilis* capable of producing digestive enzymes, for example, cellulase and/or mannase, to degrade cellulose may be used. *Bacillus subtilis* is a gram-positive, aerobic bacterium that commonly inhabits the soil, fermented soybean paste or red pepper paste. The *Bacillus subtilis* strain may be, for example, *Bacillus subtilis* CJBS62 or *Bacillus subtilis* CJBS16. Particularly, *Bacillus subtilis* CJBS62 can be used. *Bacillus subtilis* CJBS62 was deposited with the Korean Culture Center of Microorganisms (KCCM) (Yurim Building 45, Hongjenae-2ga-Gil, Seodaemun-Ku, Seoul, Korea) on Jun. 22, 2017 and received deposit number KCCM12039P. The sequence (5'→3') of 16 s ribosomal DNA of the *Bacillus subtilis* CJBS62 is set forth in SEQ ID NO. 3.

Any strain belonging to *Bacillus licheniformis* capable of degrading lactate to acetate may be used. When cultured in a lactate-containing medium for 9 to 48 hours, the *Bacillus licheniformis* strain can convert 30% to 70%, specifically 50% to 65%, of the initial amount of lactate to acetate or can convert at least 50%, at least 60%, at least 70% or at least 80% of the consumed amount of lactate to acetate. The conversion rate of the initial amount of lactate to acetate and the conversion rate of the consumed amount of lactate to acetate can be calculated by Formulas 1 and 2, respectively:

Conversion rate of initial amount of lactate to acetate (%)=(Amount of acetate produced/Initial amount of lactate)*100 [Formula 1]

Conversion rate of consumed amount of lactate to acetate (%)=(Amount of acetate produced/Consumed amount of lactate)*100 [Formula 2]

The *Bacillus licheniformis* strain can additionally produce cellulase and/or mannase.

*Bacillus licheniformis* is a gram-positive, aerobic bacterium that commonly inhabits fermented soybean paste or red pepper paste. The *Bacillus licheniformis* strain may be, for example, *Bacillus licheniformis* CJBL215 or *Bacillus licheniformis* CJBL219. Particularly, *Bacillus licheniformis* CJBL219 can be used. *Bacillus licheniformis* CJBL215 or *Bacillus licheniformis* CJBL219 were deposited with the Korean Culture Center of Microorganisms (KCCM) (Yurim Building 45, Hongjenae-2ga-Gil, Seodaemun-Ku, Seoul, Korea) on Jun. 22, 2017 and received deposit numbers KCCM12040P and KCCM12041P, respectively. The sequences (5'→3') of 16 s ribosomal DNA of *Bacillus licheniformis* CJBL215 and *Bacillus licheniformis* CJBL219 are set forth in SEQ ID NOS. 1 and 2, respectively.

The feed additive comprising the *Bacillus subtilis* strain and the *Bacillus licheniformis* strain can stabilize the rumen pH of ruminants and can increase feed digestibility of ruminants. The feed additive is effective in improving milk fat production in milking cows and can efficiently increase the amount of milk produced.

The *Bacillus subtilis* strain and the *Bacillus licheniformis* strain may be each independently present at a concentration of at least $1 \times 10^7$ cfu, specifically at least $1 \times 10^8$ cfu, more specifically $1 \times 10^9$ cfu, per gram of the feed additive. The presence of the strains at the concentrations defined above makes the feed additive effective in degrading cellulose and increasing milk fat.

The feed additive may be used in an amount of 0.1 g to 1 kg, specifically 5 g to 900 g, more specifically 10 g to 800 g per head of animal per day.

The weight ratio of the *Bacillus subtilis* strain to the *Bacillus licheniformis* strain may range from 1:9 to 9:1, specifically from 2:8 to 8:2, more specifically from 3:7 to 7:3, most specifically from 1:2 to 2:1.

The feed additive may be a liquid or solid. When the feed additive is a liquid, the *Bacillus subtilis* strain and the *Bacillus licheniformis* strain may exist in the form of their biomass, culture broth or concentrate. The solid feed additive may include a biomass, culture broth or concentrate of the *Bacillus subtilis* strain and the *Bacillus licheniformis* strain. For example, the solid feed additive may take the form of a powder, tablet, pellet, granule or coating that is prepared by heat- or freeze-drying.

Another embodiment of the present invention provides a feed composition comprising the feed additive. The feed composition may include 0.1% to 50% by weight, specifically 0.1% to 40% by weight, more specifically 1% to 20% by weight of the feed additive based on the weight of the composition.

The feed composition may further include at least one ingredient selected from animal growth promotors, nutrients, nutritional supplements, storage stabilizers, and coating agents. The feed composition may include at least one ingredient selected from: other probiotics; enzymes, such as amylase and lipase; vitamins, such as L-ascorbic acid, choline chloride, and inositol; minerals, such as potassium chloride, iron citrate, magnesium oxide, and phosphates; amino acids, such as lysine, alanine, and methionine; organic acids, such as fumaric acid, butyric acid, and lactic acid, and salts thereof; antioxidants, such as vitamin C and vitamin E; antifungal agents, such as calcium propionate; emulsifying agents, such as lecithin and glycerin fatty acid esters; and colorants.

The feed may be an animal feed, specifically a ruminant feed. Examples of such ruminants include, but are not limited to, cows, water buffalo, mountain goats, sheep, goats, and deer. Intake of the feed can be appropriately determined depending on the kind, weight, age, sex, and general health of the animal, the ingredients of the feed, and other factors.

A further embodiment of the present invention provides a method for producing the feed additive. The method comprises culturing a *Bacillus subtilis* strain and a *Bacillus licheniformis* strain and drying a cultured biomass, culture broth or concentrate of the strains. Specifically, the culturing may comprise inoculating with the strains and culturing the strains at 30 to 50° C. for 2 to 60 hours, for example, at 32 to 40° C. for 5 to 50 hours. More specifically, the culturing may comprise inoculating with the strains, primarily culturing the strains at 30 to 50° C. for 2 to 60 hours, for example, at 32 to 40° C. for 5 to 50 hours until the level of the strains reaches at least $1 \times 10^7$ cfu per gram of culture broth, adding one or more raw materials selected from corn, wheat gluten, soybean meal, and sugar syrup to the primary culture, and secondarily culturing the strains at 30 to 50° C. for 2 to 60 hours, for example, at 32 to 40° C. for 5 to 50 hours. The cultured biomass, culture broth or concentrate may be dried at 40 to 70° C. for 5 to 120 hours, for example, at 40 to 60° C. for 5 to 60 hours. In one embodiment, the method may further comprise pulverizing the dried cultured biomass, culture broth or concentrate.

Yet another embodiment of the present invention provides a method for increasing milk fat and milk yield of an animal, comprising administering the feed additive comprising the *Bacillus subtilis* strain and the *Bacillus licheniformis* strain to the animal. A detailed description of this embodiment is the same as that of other embodiments described herein.

Yet another embodiment of the present invention provides a method for stabilizing the rumen pH of an animal, particularly a ruminant, comprising administering the feed additive comprising the *Bacillus subtilis* strain and the *Bacillus licheniformis* strain to the animal. A detailed description of this embodiment is the same as that of other embodiments described herein.

Yet another embodiment of the present invention provides a method for enhancing the digestibility of an animal, particularly a ruminant, comprising administering the feed additive comprising the *Bacillus subtilis* strain and the *Bacillus licheniformis* strain to the animal. A detailed description of this embodiment is the same as that of other embodiments described herein.

Advantageous Effects

The feed additive according to the present invention is helpful in improving milk fat of a ruminant and can keep milk fat from decreasing when exposed to high-temperature stress in summer. In addition, the feed additive according to the present invention is effective in degrading lactate in the rumen. Therefore, the feed additive according to the present invention can prevent the rumen pH from decreasing by lactate and thus is useful in preventing rumen acidosis.

DESCRIPTION OF DRAWINGS

FIG. 1 shows electron microscopy images of *Bacillus subtilis* CJBS62 and *Bacillus licheniformis* CJBL215 and CJBL219 isolated in one example of the present invention.

FIG. 2 shows color change of a medium used for screening a lactate-consuming strain in one example of the present invention. When the color of the medium turned from yellow (left) to purple (right), a strain in the medium was judged to consume lactate.

FIG. 3 is a histogram showing the conversion rates to acetate by strains as measured in one example of the present invention.

FIG. 4 shows the amounts of lactate consumed and acetate produced by *Bacillus licheniformis* CJBL215 and CJBL219 (left, y axis) and the conversion rates to acetate (right, x-axis) upon 9 h and 48 h culture in one example of the present invention.

FIG. 5 is an image confirming whether *Bacillus subtilis* CJBS62 and *Bacillus licheniformis* CJBL215 and CJBL219 were hemolyzed in one example of the present invention.

FIG. 6 shows culturing time-dependent changes in lactate concentration when a feed additive according to one example of the present invention was added to a concentrated feed.

FIG. 7 shows culturing time-dependent changes in acetate concentration when a feed additive according to one example of the present invention was added to a concentrated feed.

FIG. 8 compares the effect of a mixture of a feed additive according to one example of the present invention and a concentrated feed on the stabilization of pH, compared to that of a control group.

FIG. 9 is a histogram showing the effect of a mixture of a feed additive according to one example of the present invention and a concentrated feed on the improvement in digestibility.

FIG. 10 is a histogram showing the effect of a mixture of a feed additive according to one example of the present invention and a TMR feed on the improvement in digestibility.

MODE FOR INVENTION

Next, the present invention will be described in more detail with reference to examples. However, it should be noted that these examples are provided for illustration only and should not be construed in any way as limiting the invention.

Examples

Example 1: Strain Isolation and Screening (1) Sampling and Strain Isolation

Samples were collected from traditionally fermented soybean paste and pepper paste. The samples were diluted stepwise, plated on brain heart infusion (BHI) (Difco) solid media, and cultured at 37° C. for 24 h. The cultures were transferred to and cultured in fresh media. Pure strains were isolated, placed in media supplemented with 20 wt % glycerol with respect to the total weight, and stored at ≤−70° C. The strains were divided into strains with good cellulase activity and strains capable of degrading lactate to acetate by below described method.

(2) Investigation of Morphological and Biochemical Properties

First, morphological and biochemical properties of the isolated strains were investigated to identify the strains. As a result of gram staining for morphological investigation, all of the isolated strains were found to be gram positive. Electron microscopy revealed that the strains were *bacillus* sp. (FIG. 1).

The biochemical properties of the isolated strains were analyzed. To this end, the sugar fermentation patterns of the strains were analyzed using an API 50 CHB system (biomerieux Vitek, Inc., France). The results are shown in Table 1.

TABLE 1

| Sugar | Results CJBL215 | CJBL219 | CJBS62 | Sugar | Results CJBL215 | CJBL219 | CJBS62 |
|---|---|---|---|---|---|---|---|
| Control | − | − | − | Esculine | + | + | + |
| Glycerol | + | + | + | Salicine | + | + | − |
| Erythritol | − | − | − | Cellobiose | + | + | − |
| D-Arabinose | − | − | − | Maltose | + | + | + |
| L-Arabinose | + | + | + | Lactose | − | + | − |
| Ribose | + | + | + | Melibiose | − | − | − |
| D-Xylose | + | − | − | Saccharose | + | + | + |
| L-Xylose | − | − | − | Trehalose | + | + | + |
| Adonitol | − | − | − | Inulin | − | − | + |
| β Methyl-xyloside | − | − | − | Melezitose | − | − | − |
| Galactose | − | + | − | D-Raffinose | + | − | + |
| D-Glucose | + | + | + | Amidon | + | + | + |
| D-Fructose | + | + | + | Glycogen | + | + | − |
| D-Mannose | + | + | + | Xylitol | − | − | − |
| L-sorbose | − | − | − | β Gentiobiose | − | − | − |
| Rhamnose | − | + | − | D-Turanose | + | + | − |
| Dulcitol | − | − | − | D-Lyxose | − | − | − |
| Inositol | + | − | + | D-Tagatose | + | + | − |
| Mannitol | + | + | + | D-Fucose | − | − | − |
| Sorbitol | − | + | + | L-Fucose | − | − | − |
| α Methyl-D-mannoside | − | − | − | D-Arabitol | − | − | − |
| α Methyl-D-glucoside | + | + | − | L-Arabitol | − | − | − |
| N Acetyl glucosamine | − | − | − | Gluconate | − | − | − |
| Amygdaline | + | + | − | 2-keto-gluconate | − | − | − |
| Arbutin | + | + | − | 5-keto-gluconate | − | − | − |

+: Positive, −: negative

As a result of analyzing the sugar fermentation patterns of the strains, CJBL215 was found to belong to *Bacillus licheniformis* (reliability 99.7%) and CJBL219 was found to belong to *Bacillus licheniformis* (reliability 99.9%). CJBS62 was found to belong to *Bacillus subtilis/amyloliquefaciens* (reliability 99.6%).

(3) Strain Identification

For more accurate identification of the strains, molecular systematics based on DNA sequencing was carried out. For DNA sequencing, 16 s rDNA gene amplification was performed using PCR premix (Bioneer, Korea) and universal primers 27F (5' AGAGTTTGATCMTGGCTCAG 3') and 1492R (5' GGTTACCTTGTTACGACTT 3') The entire reaction solution was adjusted to 20 l and gene amplification was repeated a total of 30 times at 94° C. for 1 min, at 56° C. for 1 min, and at 72° C. for 1 min. The amplified DNA sequences were analyzed. The sequences of 16 s rDNA of the isolated strains are set forth in SEQ ID NOS. 1 to 3. As a result of the analysis, each of the sequences of CJBL215 and CJBL219 had a homology of 99% with that of *Bacillus licheniformis* and the sequence of CJBS62 had a homology of 99% with that of *Bacillus subtilis*. The isolated stains were named "*Bacillus licheniformis* CJBL215", "*Bacillus licheniformis* CJBL219", and "*Bacillus subtilis* CJBS62". The newly identified microorganisms *Bacillus licheniformis* CJBL215, *Bacillus licheniformis* CJBL219, and *Bacillus subtilis* CJBS62 were deposited with the Korean Culture Center of Microorganisms (KCCM) on Jun. 22, 2017 and received deposit numbers KCCM12040P, KCCM12041P, and KCCM12039P, respectively.

Example 2: Digestive Enzyme Activities of the Isolated Strains (1) Digestive Enzyme Activities of the Strains The complex digestive enzyme activities of the isolated bacteria derived from pastes were evaluated for mannase and cellulase as digestive enzymes. The digestive enzyme activities of the strains were measured depending on whether clear zones were formed in media containing substrate for the enzymes.

The isolated strains were cultured in brain heart infusion (BHI) (Difco) liquid media for 24 h. The resulting culture broths were collected and used as crude enzyme solution for enzyme activity analysis. The degrees of degradation of the substrate in the media were determined as follows.

1) Measurement of Mannase Activity

Matrix media (Yeast extract 3 g/L, Peptone 5 g/L, $KH_2PO_4$ 1 g/L, Agar 20 g/L, pH 5) supplemented with 1% mannan (locust bean gum, sigma, USA) were prepared. The crude enzyme solution (1.5 μl each) were dropped into the matrix media. After the reactions were allowed to proceed at 37° C. for 15-18 h, the activities of the enzymes were measured depending on whether clear zones were formed. The results are shown in Table 2.

2) Measurement of Cellulase Activity

YM media supplemented with 1% carboxymethylcellulose (CMC) substrate were prepared. The crude enzyme solution (1.5 μl each) were dropped into the substrate media. Reaction was allowed to proceed at 37° C. for 15-18 h. The reaction solutions were stained with a 0.2% Congo red solution for 30 min and bleached with a 1 M aqueous NaCl solution to measure clear zones. The activities of the enzymes were measured depending on whether clear zones were formed as a result of degradation of the substrate around the strains. The results are shown in Table 2.

Based on the results of evaluations, *Bacillus subtilis* CJBS16 and CJBS62 were found to have the best mannase activities and the best cellulase activities.

TABLE 2

| Digestive enzyme activities of the screened strains (mm) | | | | |
|---|---|---|---|---|
| | CJBS16 | CJBL215 | CJBL219 | CJBS62 |
| Mannase | 5 | 0 | 2.5 | 3.5 |
| Cellulase | 2 | 3 | 2 | 3.5 |

(2) Cellulolytic Activities of Culture Supernatants

The cellulolytic abilities of culture supernatants of the screened strains were confirmed. First, each of the strains was cultured for 24 h and centrifuged at 10,000 rpm for 5 min. The resulting supernatant was filtered through a 0.2 μm syringe filter. 20 μl of the supernatant was dropped into a medium supplemented with cellulose (carboxymethylcellulose sodium salt 10 g/L, Bacto agar 15 g/L). Reaction was allowed to proceed at 37° C. for 1 day. The reaction solution was stained with a 0.4% Congo red solution for 20 min and bleached with a 1 M NaCl solution. The size of clear zones was measured to confirm the cellulolytic ability of the culture supernatant. The results are shown in Table 3. The culture supernatant of the *Bacillus subtilis* CJBS62 was found to have the best cellulolytic activity.

TABLE 3

| Cellulolytic activities of the culture supernatants of the screened strains (mm) | | | | |
|---|---|---|---|---|
| | CJBS16 | CJBL215 | CJBL219 | CJBS62 |
| Cellulolytic activity | 16.5 | 16.5 | 14 | 24 |

Example 3: Screening of Lactate-Consuming Strains and Acetate-Producing Strains

Lactate-consuming strains were qualitatively screened by the chromogenic method using BCP after culture in media supplemented with lactate. First, media supplemented with 15 mM lactate, yeast extract 10 g/L, peptone 20 g/L, NaCl 10 g/L, and bromophenol blue (BCP) 0.0004 g/L were prepared. The media (1.5 ml each) were plated on microcentrifuge tubes and the tubes were inoculated with strains (50 μl each) pre-cultured in brain heart infusion (BHI) (Difco) media. The strains were stationary cultured in the tubes at 37° C. for 4-5 days. When the color of the medium turned from yellow to purple, the strain was preliminarily judged to consume lactate in the medium. 117 strains isolated from the samples were cultured and a total of 4 strains CJBS16, CJBL215, CJBL219, and CJBS62 were screened (FIG. 2).

Brain heart infusion (BHI) (Difco) media were inoculated with the screened CJBS16, CJBL215, CJBL219, and CJBS62 and cultured at 37° C. and 200 rpm for 16 h for activation thereof. A medium supplemented with 15 mM lactate, 10 g/L of yeast extract, 20 g/L of peptone, and 10 g/L of NaCl was inoculated with each strain (5%) and cultured at 37° C. and 200 rpm for 48 h. After completion of culture, 10% BCP was added to the culture broth to reconfirm whether lactate was consumed. As a result, the four strains were confirmed to consume lactate (the colors of the culture broths turned from yellow to purple).

Example 4: Measurement of Amounts of Lactate Consumed and Amounts of Acetate Produced (1) Measurement Amounts of Acetate Produced Brain heart infusion (BHI) (Difco) media were inoculated with the screened CJBS16, CJBL215, CJBL219, and CJBS62 and cultured at 37° C. and 200 rpm for 16 h for activation thereof. A medium supplemented with 15 mM lactate, 10 g/L of yeast extract, 20 g/L of peptone, and 10 g/L of NaCl was inoculated with each strain (5%) and cultured at 37° C. and 200 rpm for 48 h.

The culture broth was centrifuged, 0.2 ml of 25% metaphosphoric acid was added to 1 ml of the collected supernatant, followed by centrifugation at 10,000 rpm for 5 min. The collected supernatant was filtered through a 0.2 µm filter and acetate content thereof was analyzed by GC (Agilent Technologies 7890A).

The four lactate-consuming strains consumed lactate to produce acetate. The acetate contents were measured. The conversion rates were represented by Formula 1:

Conversion rate of initial amount of lactate to acetate (%)=(Amount of acetate produced/Initial amount of lactate)*100    [Formula 1]

As a result, the lactate-to-acetate conversion rate of CJBL219 was highest (59.4%) and that of CJBL215 was 44.9% (Table 4, FIG. 3).

TABLE 4

Amounts of acetate produced after consumption of lactate in media and conversion rates

| Strain No. | Acetate content (mM) | Conversion rate calculated by Formula 1 (%) |
| --- | --- | --- |
| CJBL219 | 8.91 | 59.4 |
| CJBL215 | 6.74 | 44.9 |
| CJBS16 | 3.74 | 24.9 |
| CJBS62 | 1.99 | 13.3 |

(2) Measurements of Amounts of Lactate Consumed and Amounts of Acetate Produced by the Screened Strains The amounts of lactate consumed and acetate produced by the screened strains in media were quantified.

Brain heart infusion (BHI) (Difco) media were inoculated with the screened CJBS16, CJBL215, CJBL219, and CJBS62 and cultured at 37° C. and 200 rpm for 16 h for activation thereof.

A medium supplemented with 15 mM lactate, 10 g/L of yeast extract, 20 g/L of peptone, and 10 g/L of NaCl was inoculated with each strain (5%) and cultured at 37° C. and 200 rpm for 48 h. At 9 h and 48 h after initiation of culture, samples were collected.

1) Quantification of Lactate

Each culture broth was centrifuged and the collected supernatant was filtered through a 0.2 µm filter. After filtration, the culture supernatant was placed in a microcentrifuge tube and lactate content thereof was measured using a lactate bio. test kit for Cedex Bio Analyzer (ROCHE). The results are shown in Table 5.

2) Quantification of Acetate

Each culture broth was centrifuged, 0.2 ml of 25% metaphosphoric acid was added to 1 ml of the collected supernatant, followed by centrifugation at 10,000 rpm for 5 min. The collected supernatant was filtered through a 0.2 µm filter and acetate content thereof was analyzed by GC (Agilent Technologies 7890A). The results are shown in Table 5 and FIGS. 4 and 5.

Conversion rate of consumed amount of lactate to acetate (%)=(Amount of acetate produced/Consumed amount of lactate)*100    [Formula 2]

Referring to table 5, CJBL215 consumed 49.8% of the initial amount of lactate during culture for 48 h and converted about 91.1% of the consumed lactate to acetate. CJBL219 consumed 48.6% of the initial amount of lactate during culture for 48 h and converted all consumed lactate to acetate (FIG. 4).

TABLE 5

Contents of lactate and acetate in media at different time points during culture and conversion rates

| | | 0 h | 9 h | 48 h |
| --- | --- | --- | --- | --- |
| CJBL215 | Lactate amount (mM) | 13.12 | 8.35 | 6.59 |
| | Acetate amount (mM) | 0 | 2.50 | 5.94 |
| | Conversion rate calculated by Formula 2 (%) | | 52.4 | 91.1 |
| CJBL 219 | Lactate amount (mM) | 13.12 | 8.52 | 6.74 |
| | Acetate amount (mM) | 0 | 2.87 | 6.49 |
| | Conversion rate calculated by Formula 2 (%) | | 62.4 | 101.8 |

Example 5: Stability of the Strains (1) Confirmation of Hemolysis of the Strains β-Hemolysis refers to a phenomenon in which phospholipids supplied by erythrocytes are hydrolyzed by phospholipase produced from harmful bacteria, resulting in hemolysis of erythrocytes. Hemolysis of the isolated strains was investigated using blood agar plate media (sheep blood 5%, Hanil Komed Co. Ltd., Korea). The strains were streaked onto the blood agar plate media and cultured at 37° C. for 24 h. An observation was made as to whether hemolysis occurred. No hemolysis was observed, as shown in FIG. 5.

(2) Confirmation of Susceptibilities of the Strains to Antibiotics

The susceptibilities of the screened strains to antibiotics were confirmed by the following procedure. First, brain heart infusion (BHI) (Difco) media were inoculated with the screened strains and cultured at 37° C. and 200 rpm for 16 h. Sterile cotton swabs soaked with the cultured strains were used to plate the strains on Mueller Hinton II Agar plates (Difco). Antibiotic discs were placed on the plate media, followed by culture at 37° C. for 15-18 h. Ampicillin, clindamycin, gentamicin, kanamycin, tetracycline, vancomycin, erythromycin, ampicillin/sulbactam, chloramphenicol, and streptomycin discs (OXOID) were prepared for antibiotic testing. The susceptibilities of the strains to the antibiotics were confirmed depending on the formation of clear zones around the antibiotic discs after culture. As a result of the antibiotic susceptibility tests, the screened strains were found to be less resistant to the antibiotics (Table 6).

TABLE 6

Degrees of growth inhibition of the strains by antibiotics

| | Radii of clear zones around antibiotics (mm) | | |
| --- | --- | --- | --- |
| Antibiotics | CJBL215 | CJBL219 | CJBS62 |
| Amp10 (Ampicillin) | 10 | 8 | 10 |
| C30 (Clindamycin) | 14 | 4 | 9 |
| CN120 (Gentamicin) | 18 | 12 | 12 |

TABLE 6-continued

Degrees of growth inhibition of the strains by antibiotics

| | Radii of clear zones around antibiotics (mm) | | |
|---|---|---|---|
| Antibiotics | CJBL215 | CJBL219 | CJBS62 |
| K30 (Kanamycin) | 13 | 9 | 10 |
| TE30 (Tetracycline) | 5 | 8 | 12 |
| VA30 (Vancomycin) | 9 | 6 | 7 |
| E15 (Erythromycin) | 13 | 13 | 11 |
| SAM20 (Ampicillin/Sulbactam) | 15 | 12 | 13 |
| S10 (Chloramphenicol) | 3 | 3 | 6 |
| DA2 (Streptomycin) | 6 | 7 | 9 |

Example 6: Preparation of Feed Additive Including the Strains

9 L of tryptic soy broth was inoculated with each of the *bacillus* strains CJBL215, CJBL219, and CJBL62 (two species of *Bacillus licheniformis* and one species of *Bacillus subtilis*) and cultured at 36° C. for 36 h.

The strain was plated on a tryptic soy agar medium and the number of colonies was measured. At that time, the strain was cultured until the number of colonies reached $\geq 1\times 10^9$ cfu per gram of strain. A mixture of 20 kg of corn, 30 kg of wheat gluten, 45 kg of soybean meal, and 5 kg of sugar syrup was prepared as a raw material for solid state fermentation. The culture broths of the three species of *bacillus* strains (9 L each) were mixed together. The mixture of the culture broths (total 27 L) was added to 100 kg of the raw material for solid state fermentation. The strains were homogenously fermented with stirring in the raw material for solid state fermentation at a temperature of 34° C. for 48 h. After the fermentation was finished, the mixture was dried at a temperature of 50° C. for 48 h and pulverized to produce a feed additive.

Example 7: Effect of the Feed Additive on the Fermentation Behavior in the Rumen Depending on Matrices Tests were conducted to investigate the effect of the feed additive on the improvement of dry matter digestibility and the enhancement of acetate using a stationary culture system in a rumen model.

Treatment group: 50 mg of the feed additive produced in Example 6 and 0.5 g of a matrix were fed into a 200 ml serum bottle. 37.5 ml of a buffer reduced by carbon dioxide gas and 12.5 ml of a rumen fluid were maintained in an anaerobic state using carbon dioxide gas. After the serum bottle was filled with carbon dioxide gas for ~30 sec, the inlet of the serum bottle was closed with a septum, the serum bottle was sealed with an aluminum cap, followed by culture in a stationary incubator at 39° C. for 24 h. At that time, a concentrated feed or total mixed ration (TMR) was used as the matrix. The feed additive was added in an amount of 10 wt % per 0.5 g of the matrix. The buffer was prepared by mixing 9.3 g/L sodium phosphate monobasic ($NaH_2PO_4\cdot 2H_2O$), 9.8 g/L sodium bicarbonate ($NaHCO_3$), 0.47 g/L sodium chloride (NaCl), 0.57 g/L potassium chloride (KCl), 0.256 g/L magnesium chloride ($MgCl_2$), 0.106 g/L calcium chloride ($CaCl_2$), 2.5 g/L casein (N-Z-Amine), and 1.25 ml/L resazurin solution.

Control group: The strains were cultured under the same conditions as in the treatment group, except that the feed additive was not added.

Each of the treatment group and the control group was cultured in a stationary incubator at 39° C. and lactate content thereof, acetate content, pH, and dry matter digestibility were measured by the following methods:

Each of the culture broths was centrifuged and the collected supernatant was filtered through a 0.2 µm filter. After filtration, the culture supernatant was placed in a microcentrifuge tube and lactate content thereof was measured using a lactate bio. test kit for Cedex Bio Analyzer (ROCHE). Each culture broth was centrifuged, 0.2 ml of 25% metaphosphoric acid was added to 1 ml of the collected supernatant, followed by centrifugation at 10,000 rpm for 5 min. The collected supernatant was filtered through a 0.2 m filter and acetate content thereof was analyzed by GC (Agilent Technologies 7890A). Dry matter digestibility was calculated by Formula 3:

$$\text{Dry matter digestibility (\%)} = (\text{Amount of matrix before culture} - \text{Amount of matrix after culture})/\text{Amount of matrix before culture}*100 \quad [\text{Formula 3}]$$

The amount of the matrix before culture and the amount of the matrix after culture were measured after filtration of the culture broth through filter paper using a vacuum pump and drying at 60° C. overnight.

Changes in the concentration of lactate and acetate in the treatment group and the control group were measured at different time points during culture. The results are shown in FIGS. 6 and 7.

Referring to FIG. 6, the minimum concentration of lactate in the treatment group was ~10% lower than in the control group. Referring to FIG. 7, the maximum concentration of acetate in the treatment group was ~2.5 times that in the control group.

The pH values and the dry matter digestibility values (%) of the treatment group and the control group are shown in FIGS. 8, 9, and 10 (respectively).

Referring to FIG. 8, the pH of the control group was 0.5 lower than its initial value while the pH of the treatment group was 0.42 lower than its initial value. These results indicate that the feed additive according to the present invention is effective in stabilizing the rumen.

Referring to FIGS. 9 and 10, the dry matter digestibility values of the treatment group using the concentrated feed and the TMR matrices were measured to be higher by 4% and 1.3% than those of the control group, respectively. In conclusion, the feed additive according to the present invention can improve the digestibility in the rumen and can increase the production of acetate, indicating positive influence on increase of milk fat.

Example 8: Effect of the Feed Additive for Enhancing Milk Fat on Milk Productivity of Milking Cows The feed additive according to the present invention was produced by the method mentioned in Example 6 and was used for feed testing on milking cows. The influence of the feed additive on the milk productivity of milking cows was evaluated through a known dairy feed test method. First, 72 milking cows were divided into a control group and a treatment group, 36 cows per group. A conventional feed was administered to the control group for a test period of 4 weeks and a mixture of the feed additive according to the present invention and the conventional feed in the form of a top-dressing was fed to the treatment group (each 20 g per head of animal per day). Before initiation of feeding and after feeding, the amounts of milk fat and milk protein and milk yields were measured. The results are shown in Tables 7, 8, and 9.

As a result of continuous feeding of the feed additive to the milking cows (each 20 g per head of animal per day), milk fat was increased by 0.3% p, as shown in Table 7. As can be seen from the results in Table 8, the control group showed no change in the level of milk protein but the treatment group showed a significant improvement in the level of milk protein (0.1% p). No significant change in milk yield was observed in the control group but a significant increase in milk yield (0.4 kg) was observed in the treatment group (Table 9).

The above results conclude that the feed additive according to the present invention has a positive influence on the improvement of milk fat, milk protein, and milk yield, achieving high productivity and quality of milk from milking cows.

TABLE 7

Effect of the feed additive on improvement in milk fat

|  | Control group | Treatment group |
|---|---|---|
| Before initiation (average for 3 weeks) | 4.7% | 4.7% |
| After feeding (average for 4 weeks) | 4.7% | 5.0% |
| Increment in milk fat (% p) | 0.0 | 0.3 |

TABLE 8

Effect of the feed additive on improvement in milk protein

|  | Control group | Treatment group |
|---|---|---|
| Before initiation (average for 3 weeks) | 3.4% | 3.2% |
| After feeding (average for 4 weeks) | 3.4% | 3.3% |
| Increment in milk protein (% p) | 0.0 | 0.1 |

TABLE 9

Effect of the feed additive on improvement in milk yield

|  | Control group | Treatment group |
|---|---|---|
| Before initiation (average for 3 weeks) | 27.9 kg | 31.9 kg |
| After feeding (average for 4 weeks) | 28.0 kg | 32.3 kg |
| Increment in milk yield (kg) | 0.1 | 0.4 |

Example 9: Effect of the Feed Additive for Enhancing Milk Fat on the Productivity of Milking Cows when Exposed to High-Temperature Stress in Summer The feed additive according to the present invention was produced by the method mentioned in Example 6 and was used for feed testing on milking cows. The influence of the feed additive on the milk productivity of milking cows was evaluated through a known dairy feed test method. First, a feed including 0.2 wt % of the feed additive according to the present invention was fed to 150 milking cows over 4 weeks (from May 26 to June 23), which is a common period for which dairy cattle are exposed to a high-temperature stress environment. The productivities of milk from the milking cows before and after feeding were compared.

For a control group, a feed without the feed additive was fed to the milking cows over 4 weeks in an environment without high-temperature stress. For a treatment group, a feed including 0.2 wt % of the feed additive was fed to the milking cows in a high-temperature stress environment over 4 weeks. The basic composition of the feed fed to the treatment group was the same as that of the feed fed to the control group.

TABLE 10

Effect of the feed additive on the productivity of milk in summer

|  | Milk fat | Milk yield |
|---|---|---|
| Control group | 3.7% | 36.2 kg |
| Treatment group | 3.9% | 36.7 kg |
| Increment | 0.2% p | 0.5 kg |

Referring to Table 10, the milk fat and milk yield measured in the treatment group were found to be higher by 0.2% p and 0.5 kg than those measured in the control group, respectively.

It is generally known that exposure of milking cows to a high-temperature stress environment decreases milk yield and milk fat produced from milking cows. However, feeding of the feed additive according to the present invention to milking cows can improve milk fat and milk yield even when exposed to a high-temperature stress environment.

The invention claimed is:

1. A method for increasing milk fat and milk yield, stabilizing rumen pH, and enhancing digestibility of a ruminant comprising:

administering a feed additive comprising a *Bacillus subtilis* strain and a *Bacillus licheniformis* strain to the ruminant, wherein the *Bacillus subtilis* strain is *Bacillus subtilis* CJBS62 (KCCM12039P), wherein the *Bacillus licheniformis* strain is selected from the group consisting of *Bacillus licheniformis* CJBL215 (KCCM12040P) and *Bacillus licheniformis* CJBL219 (KCCM12041P), and wherein the *Bacillus licheniformis* strain produces acetate when cultured in a lactate-containing medium for 9 to 48 hours and converts 30% to 70% of the initial amount of lactate to acetate.

2. The method according to claim 1, wherein the *Bacillus subtilis* strain and the *Bacillus licheniformis* strain are each independently present at a concentration of at least $1\times10^7$ cfu per gram of the feed additive.

3. The method according to claim 1, wherein the *Bacillus subtilis* strain and the *Bacillus licheniformis* strain are blended in a weight ratio of 1:9 to 9:1.

* * * * *

SEQUENCE LISTING

<160> NUMBER OF SEQ ID NOS: 3

<210> SEQ ID NO 1
<211> LENGTH: 1506
<212> TYPE: DNA
<213> ORGANISM: Artificial Sequence
<220> FEATURE:
<223> OTHER INFORMATION: CJBL215 16s rDNA

<400> SEQUENCE: 1

```
tcaccttttt cgggtttccc ctttacgact tcaccccaat catctgtccc accttcggcg      60
gctggctcca aaaggttacc tcaccgactt cgggtgttac aaactctcgt ggtgtgacgg     120
gcggtgtgta caaggcccgg gaacgtattc accgcggcat gctgatccgc gattactagc     180
```

```
gattccagct tcacgcagtc gagttgcaga ctgcgatccg aactgagaac agatttgtgg      240
gattggctta gcctcgcggc ttcgctgccc tttgttctgc ccattgtagc acgtgtgtag      300
cccaggtcat aagggcatg atgatttgac gtcatcccca ccttcctccg gtttgtcacc       360
ggcagtcacc ttagagtgcc caactgaatg ctggcaacta agatcaaggg ttgcgctcgt      420
tgcgggactt aacccaacat ctcacgacac gagctgacga caaccatgca ccacctgtca      480
ctctgccccc gaaggggaag ccctatctct agggttgtca gaggatgtca agacctggta     540
aggttcttcg cgttgcttcg aattaaacca catgctccac cgcttgtgcg ggccccgtc       600 aattcctttg agtttcagtc ttgcgaccgt actccccagg cggagtgctt aatgcgtttg      660
ctgcagcact aaagggcgga acccctctaa cacttagcac tcatcgttta cggcgtggac      720
taccagggta tctaatcctg ttcgctcccc acgctttcgc gcctcagcgt cagttacaga     780
ccagagagtc gccttcgcca ctggtgttcc tccacatctc tacgcatttc accgctacac      840
gtggaattcc actctcctct tctgcactca agttccccag tttccaatga ccctccccgg      900
ttgagccggg ggctttcaca tcagacttaa gaaaccgcct gcgcgcgctt tacgcccaat     960
aattccggac aacgcttgcc acctacgtat taccgcggct gctggcacgt agttagccgt     1020
ggctttctgg tcaggtaccg tcaaggtacc gccctattcg aacggtactt gttcttccct     1080
aacaacagag ttttacgatc cgaaaaccctt catcactcac gcggcgttgc tccgtcagac    1140
tttcgtccat tgcggaagat tccctactgc tgcctcccgt aggagtctgg gccgtgtctc     1200
agtcccagtg tggccgatca ccctctcagg tcggctacgc atcgttgcct tggtgagccg     1260
ttacctcacc aactagctaa tgcgccgcgg gtccatctgt aagtggtagc taaaagccac     1320
cttttatgtt tgaaccatgc ggttcaaaca agcatccggt attagcccg gtttcccgga     1380 gttatcccag tcttacaggc aggttaccca cgtgttactc acccgtccgc cgctaacatc     1440
agggagcaag ctcccatctg tccgctcgac ttgcatgtat taggcacgcc gccagcgttc     1500
gtctga                                                                1506

<210> SEQ ID NO 2
<211> LENGTH: 1504
<212> TYPE: DNA
<213> ORGANISM: Artificial Sequence
<220> FEATURE:
<223> OTHER INFORMATION: CJBL219 16s rDNA

<400> SEQUENCE: 2 tttttttccgg tttccccttt acgacttcac cccaatcatc tgtcccacct tcggcggctg     60
gctccaaaag gttacctcac cgacttcggg tgttacaaac tctcgtggtg tgacgggcgg    120
tgtgtacaag gcccgggaac gtattcaccg cggcatgctg atccgcgatt actagcgatt     180
ccagcttcac gcagtcgagt tgcagactgc gatccgaact gagagcagat tgtgggatt      240 ggcttagcct cgcggcttcg ctgcccttg ttctgcccat gtagcacgt gtgtagccca       300 ggtcataagg ggcatgatga tttgacgtca tccccacctt cctccggttt gtcaccggca     360
gtcaccttag agtgcccaac tgaatgctgg caactaagat caagggttgc gctcgttgcg     420
ggacttaacc caacatctca cgacacgagc tgacgacaac catgcaccac ctgtcactct     480 gccccgaag gggaagccct atctctaggg gtgtcagagg atgtcaagac ctggtaaggt      540
tcttcgcgtt gcttcgaatt aaaccacatg ctccaccgct tgtgcgggcc ccgtcaatt     600 cctttgagtt tcagtcttgc gaccgtactc cccaggcgga gtgcttaatg cgtttgctgc     660
```

| | |
|---|---|
| agcactaaag ggcggaaacc ctctaacact tagcactcat cgtttacggc gtggactacc | 720 |
| agggtatcta atcctgttcg ctccccacgc tttcgcgcct cagcgtcagt tacagaccag | 780 |
| agagtcgcct tcgccactgg tgttcctcca catctctacg catttcaccg ctacacgtgg | 840 |
| aattccactc tcctcttctg cactcaagtt ccccagtttc caatgaccct ccccggttga | 900 |
| gccgggggct ttcacatcag acttaagaaa ccgcctgcgc gcgctttacg cccaataatt | 960 |
| ccggacaacg cttgccacct acgtattacc gcggctgctg cacgtagtt agccgtggct | 1020 |
| ttctggttag gtaccgtcaa ggtaccgccc tgttcgaacg gtacttgttc ttccctaaca | 1080 |
| acagagtttt acgatccgaa accttcatc actcacgcgg cgttgctccg tcagactttc | 1140 |
| gtccattgcg gaagattccc tactgctgcc tcccgtagga gtctgggccg tgtctcagtc | 1200 |
| ccagtgtggc cgatcaccct tcaggtcggc tacgcatcg tcgccttggt gagccgttac | 1260 |
| ctcaccaact agctaatgcg ccgcgggtcc atctgtaagt ggtagctaaa agccacctt | 1320 |
| tataattgaa ccatgcggtt caatcaagca tccggtatta gccccggttt cccggagtta | 1380 |
| tcccagtctt acaggcaggt tacccacgtg ttactcaccc gtccgccgct aacctaaggg | 1440 |
| agcaagctcc cgtcggttcg ctcgacttgc atgtattagg cacgccgcca gcgttcgtcc | 1500 |
| tgac | 1504 |

<210> SEQ ID NO 3
<211> LENGTH: 1490
<212> TYPE: DNA
<213> ORGANISM: Artificial Sequence
<220> FEATURE:
<223> OTHER INFORMATION: CJBS62 16s rDNA

<400> SEQUENCE: 3

| | |
|---|---|
| cccccttacga cttcaccccca atcatctgtc ccaccttcgg cggctggctc ctaaaaggtt | 60 |
| acctcaccga cttcgggtgt tacaaactct cgtggtgtga cgggcggtgt gtacaaggcc | 120 |
| cgggaacgta ttcaccgcgg catgctgatc cgcgattact agcgattcca gcttcacgca | 180 |
| gtcgagttgc agactgcgat ccgaactgag aacagatttg tgggattggc ttaacctcgc | 240 |
| ggtttcgctg cccttttgttc tgtccattgt agcacgtgtg tagcccaggt cataaggggc | 300 |
| atgatgattt gacgtcatcc ccaccttcct ccggtttgtc accggcagtc accttagagt | 360 |
| gcccaactga atgctggcaa ctaagatcaa gggttgcgct cgttgcggga cttaacccaa | 420 |
| catctcacga cacgagctga cgacaaccat gcaccacctg tcactctgcc cccgaagggg | 480 |
| acgtcctatc tctaggattg tcagaggatg tcaagacctg gtaaggttct tcgcgttgct | 540 |
| tcgaattaaa ccacatgctc caccgcttgt gcgggccccc gtcaattcct ttgagtttca | 600 |
| gtcttgcgac cgtactcccc aggcggagtg cttaatgcgt tagctgcagc actaaggggc | 660 |
| ggaaacccc taacacttag cactcatcgt ttacggcgtg gactaccagg gtatctaatc | 720 |
| ctgttcgctc cccacgcttt cgctcctcag cgtcagttac agaccagaga gtcgccttcg | 780 |
| ccactggtgt tcctccacat ctctacgcat ttcaccgcta cacgtggaat tccactctcc | 840 |
| tcttctgcac tcaagttccc cagtttccaa tgaccctccc cggttgagcc ggggctttc | 900 |
| acatcagact taagaaaccg cctgcgagcc ctttacgccc aataattccg gacaacgctt | 960 |
| gccacctacg tattaccgcg gctgctggca cgtagttagc cgtggctttc tggttaggta | 1020 |
| ccgtcaaggt accgccctat cgaacggta cttgttcttc cctaacaaca gagctttacg | 1080 |
| atccgaaaac cttcatcact cacgcggcgt tgctccgtca gacttcgtc cattgcggaa | 1140 |
| gattccctac tgctgcctcc cgtaggagtc tgggccgtgt ctcagtccca gtgtggccga | 1200 |

```
tcaccctctc aggtcggcta cgcatcgtcg ccttggtgag ccgttacctc accaactagc    1260
taatgcgccg cgggtccatc tgtaagtggt agccgaagcc accttttatg tttgaaccat    1320
gcggttcaaa caaccatccg gtattagccc cggtttcccg gagttatccc agtcttacag    1380
gcaggttacc cacgtgttac tcacccgtcc gccgctaaca tcagggagca agctcccatc    1440
tgtccgctcg acttgcatgt attaggcacg ccgccagcgt tcgtctgacg              1490
```